United States Patent [19]
Oswald et al.

[11] 3,979,483
[45] Sept. 7, 1976

[54] ASYMMETRIC OS-DIALKYL-O-[(METHOXYPHENYL)-VINYL]-THIOPHOSPHATES

[75] Inventors: Alexis A. Oswald, Mountainside; Paul L. Valint, Woodbridge, both of N.J.

[73] Assignee: Ciba-Geigy AG, Basel, Switzerland

[22] Filed: Feb. 26, 1975

[21] Appl. No.: 553,335

Related U.S. Application Data

[62] Division of Ser. No. 373,723, June 26, 1973, Pat. No. 3,878,268.

[30] Foreign Application Priority Data
June 27, 1972 Switzerland............... 9609/72

[52] U.S. Cl................................. 260/951; 424/217
[51] Int. Cl.²..................... C07F 9/165; A01N 9/36
[58] Field of Search.................................. 260/951

[56] References Cited
UNITED STATES PATENTS
3,116,201 12/1963 Whetstone et al............. 260/951 X

*Primary Examiner*—Anton H. Sutto
*Attorney, Agent, or Firm*—Frederick H. Rabin

[57] ABSTRACT

Compounds of the formula

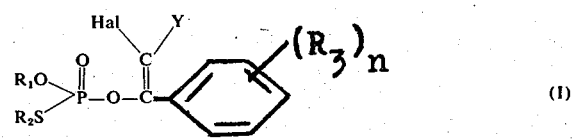

wherein
- $R_1$ represents methyl or ethyl,
- $R_2$ represents propyl or butyl, preferably n-propyl, or isobutyl,
- $(R_3)_n$ represents one or more hydrogen atoms, or represents similar or different chlorine, bromine, methyl or methoxy, $n$ is 1, 2 or 3,
- Y represents hydrogen or chlorine and Hal represents chlorine or bromine and their use for combating insects and members of the order Acarina are disclosed.

10 Claims, No Drawings

ASYMMETRIC OS-DIALKYL-O-[(METHOXYPHENYL)-VINYL]-THIOPHOSPHATES

This is a division of application Ser. No. 373,723, filed on June 26, 1973, now U.S. Pat. No. 3,878,268.

The present invention relates to O-1-phenyl-2-halovinylthio- and dithio-phosphoric acid esters, processes for their manufacture, and to their use in pest control.

The compounds have the formula

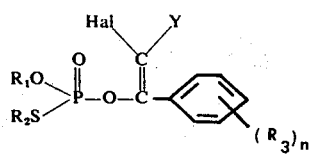

(I)

wherein $R_1$ represents methyl or ethyl,
$R_2$ represents propyl or butyl, preferably n-propyl, or isobutyl
$(R_3)_n$ represents one or more hydrogen atoms, or represents similar or different chlorine, bromine, methyl or methoxy, $n$ is 1, 2 or 3,
Y represents hydrogen or chlorine and Hal represents chlorine or bromine.

Preferred compounds on account of their action are those of the formula I, wherein $R_1$ represents methyl or ethyl, $R_2$ represents n-propyl, or isobutyl, $R_3$ represents hydrogen, chlorine, bromine, methyl or methoxy, $n$ is 1, 2 or 3, Y represents hydrogen or chlorine and Hal represents chlorine or bromine.

Particularly preferred compounds are those of the formula I, wherein $R_1$ represents ethyl, $R_2$ represents n-propyl, or isobutyl, $R_3$ represents hydrogen or chlorine, $n$ is 1, 2 or 3, Y represents hydrogen or chlorine and Hal represents chlorine.

The compounds of the formula I are manufactured by the following methods:

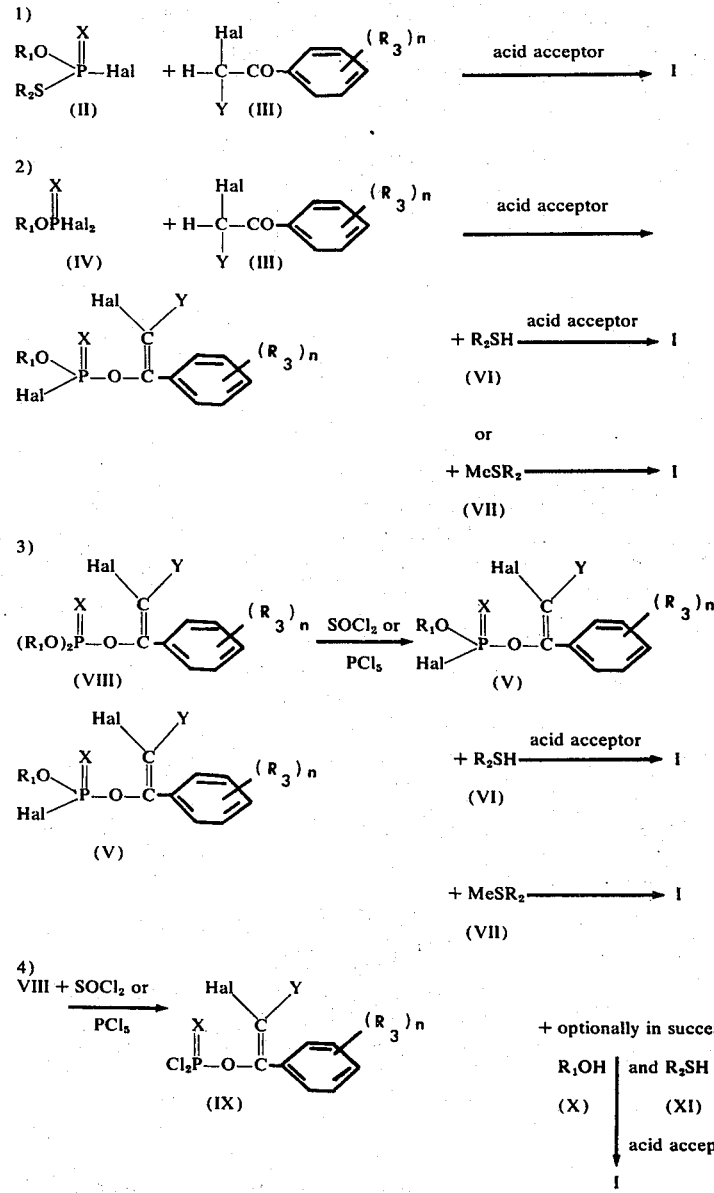

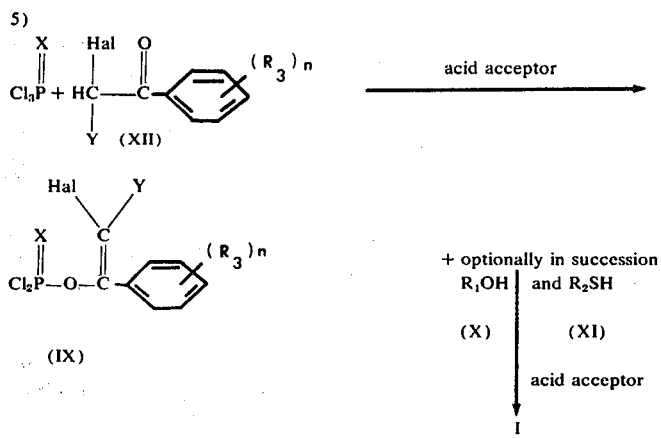

5)

+ optionally in succession
$R_1OH$ | and $R_2SH$ (X) | (XI)

acid acceptor

↓

I

In the formulae II to XII, $R_1$, $R_2$, $R_3$ X, Y, $n$, and Hal have the meanings given for the formula I and Me represents an alkali metal, in particular sodium or potassium, ammonium or $(C_1-C_4\text{-alkyl})_3$ammonium.

Suitable acid acceptors are: tertiary amines, e.g. trialkylamines, pyridine, dialkyl anilines; inorganic bases, e.g. hydroxides; carbonates and bicarbonates of alkali metals and alkaline earth metals.

Processes 1 to 5 are carried out at a reaction temperature between −10° to 100°C, in particular between 20°–80°C, at normal or elevated pressure, and in solvents or diluents.

Examples of suitable solvents or diluents are: ether and ethereal compounds, e.g. diethyl ether, dipropyl ether dioxan, dimethoxy ethane, tetrahydrofuran; amides, e.g. N,N-dialkylated carboxylic acid amides; aliphatic, aromatic and halogenated hydrocarbons, in particular benzene, toluene, xylene, chloroform, chlorobenzene; nitriles, e.g. acetonitriles; sulphoxides, e.g. dimethyl-suphoxide, ketones, e.g. acetone, methyl ethyl ketone.

Some of the starting materials of the formulae II, III, IV, VIII, IX, and XII are known or can be manufactured by methods analogous to known ones.

The compounds of the formula I have a broad biocidal activity spectrum and can therefore be used for combating various plant and animal pests. In particular they are suitable for combating insects of the families: Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Tineidae, Noctuidae, Lymantriidae, Pyralidae, Galleriidae, Culicidae, Tipulidae, Stomoxydae, Muscidae, Calliphoridae, Trypetidae, Pulicidae, as well as Acaridae of the families: Ixodidae, Argasidae, Tetranychidae, Dermanyssidae.

By addition of other insecticides and/or acaricides, e.g. those listed in German Offenlegungsschrift No. 2.248.307, pages 6 to 10, it is possible to improve substantially the insecticidal or acaricidal action and to adapt it to given circumstances.

Furthermore, the new compounds of the formula I act against plant parasitic nematodes.

The compounds of the formula I may be used as pure active substance or together with suitable carriers and-/or additives. Suitable carriers and additives can be solid or liquid and correspond to the substances conventionally used in formulation technique such, for example, as solvents, dispersants, wetting agents, adhesives, thickeners, binders and/or fertilisers.

For application, the compounds of the formula I may be processed to dusts, emulsion concentrates, granules, dispersions, sprays, to solutions, or suspensions, in the conventional formulation which is commonly employed in application technology. Mention may also be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may take, and be used in, the application forms described in German Offenlegungsschrift No. 2.248.307 on pages 12 to 18.

EXAMPLE 1

While stirred, 27, 7 g O-ethyl-S-propylchlorothiophosphate are added dropwise to a suspension of 6.25 g of NaH (50% oil suspension) in 150 ml of tetrahydrofuran. Then, while stirring, 30.7 g of 2-chloro-2',4'-dichloro-acetophenone are added dropwise over the course of 1½ hours at 25°–30°C. The reaction mixture is stirred for 3 hours at room temperature and for 1 hour at 40°–45°C. After carefully destroying the excess sodium hydride with 20 ml of absolute ethyl alcohol, the reaction mixture is diluted with 400 ml of water, the active substance extracted with benzene, and the benzene solution washed with water. The benzene is distilled off after the drying with $Na_2SO_4$, to yield the compound of the formula

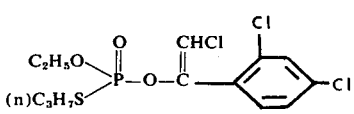

with a boiling point of 150°C/0,02 Torr.

The following compounds are also manufactured in analagous manner:

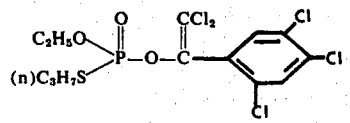 b.p.: 130°C/0.001 Torr
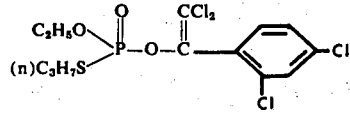 $n_D^{23}$: 1.5505
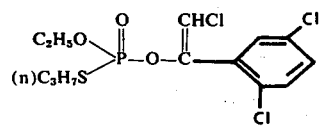 b.p.: 150°C/0.02 Torr
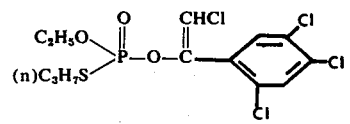 $n_D^{22}$: 1.5400
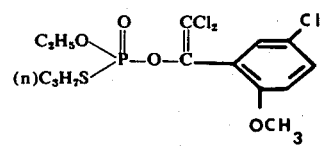 $n_D^{24}$: 1.5073
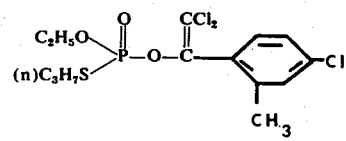 $n_D^{25}$: 1.5278
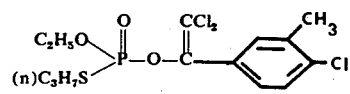 $n_D^{25}$: 1.5317
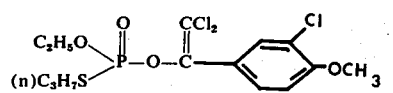 $n_D^{25}$: 1.5446
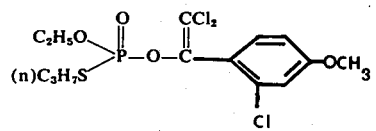 $n_D^{25}$: 1.5332

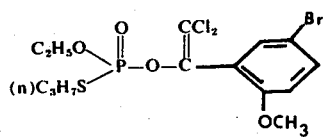 $n_D^{24}$: 1,5281
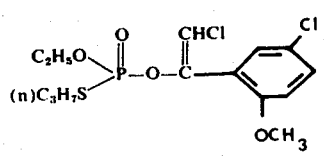 $n_D^{25}$: 1,550
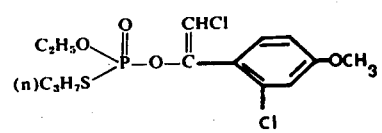 $n_D^{25}$: 1,4687
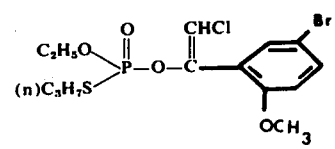 $n_D^{25}$: 1,5651
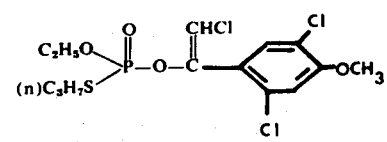 $n_D^{25}$: 1,5529
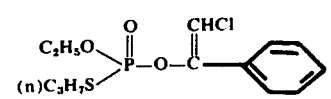 b.p.: 155°C/0,05 Torr
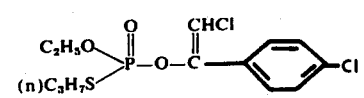 b.p.: 150°C/0,001 Torr
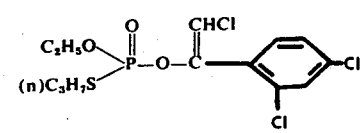 b.p.: 150°C/0,02 Torr
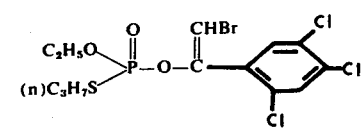 $n_D^{23}$: 1,5482

-continued
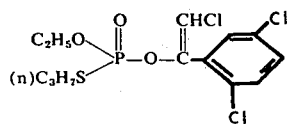
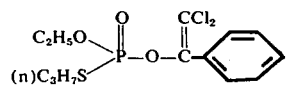
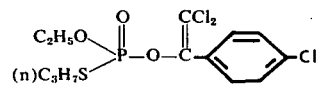
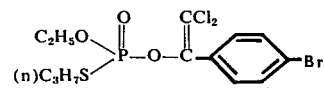
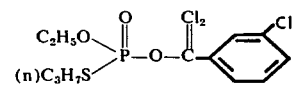
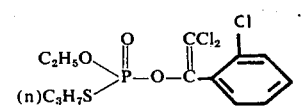
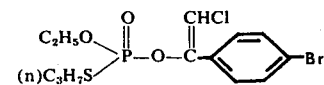
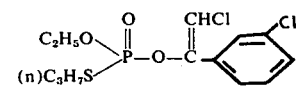
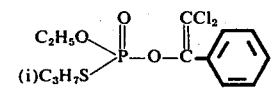
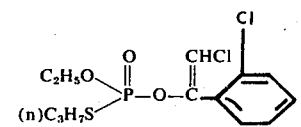
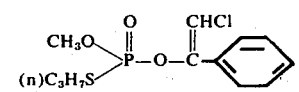
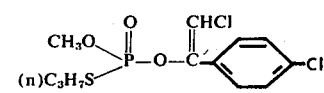
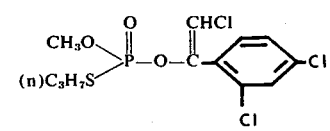
b.p.: 152°C/0.03 Torr

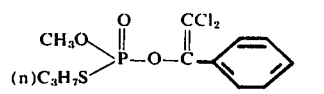
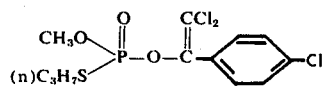
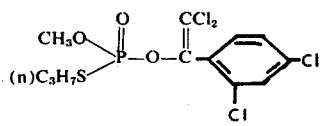
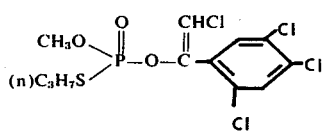
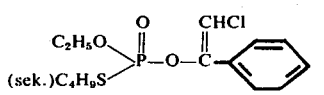
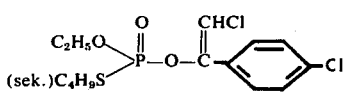
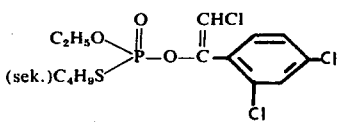
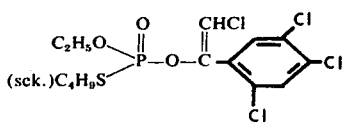
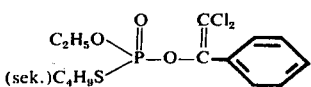
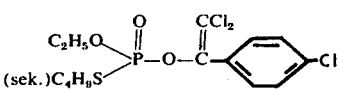
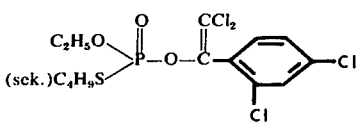
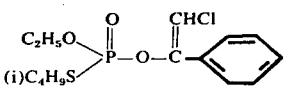
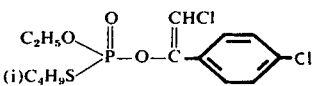

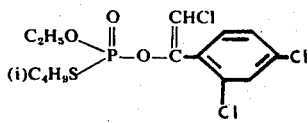

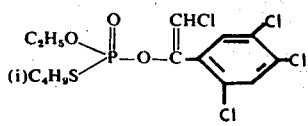

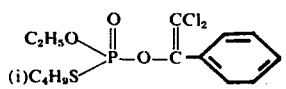

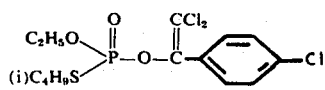

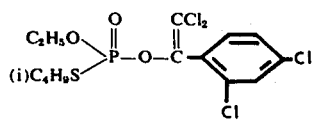

EXAMPLE 2

A. Insecticidal ingest poison action

Tobacco and potato plants were sprayed with a 0.05% aqueous emulsion (obtained from a 10% emulsifiable concentrate).

After the coating had dried, the tobacco plants were populated with *Spodoptera littoralis* and *Heliothis virescens* larvae $L_3$ and the potato plants with Colorado potato bettle larvae (*Leptinotarsa decemlineata*). The test was carried out at 24°C and 60% relative humidity. In the above test, the compounds according to Example 1 displayed good ingest poison action against *Spodoptera littoralis*, *Heliothis virescens*, and *Leptinotarsa decemlineata*.

B. Insecticidal contact action

One day before application, broad beans (*Vivia faba*) which been reared in pots were infected with about 200 leaf-lice (*Aphis fabae*) per plant. The application was effected with a compressed air spray to the leaves populated with the lice with a spray broth in a concentration of 1000 ppm (manufactured from a 25% wettable powder).

Evaluation took place 24 hours after the application. The compounds according to Example 1 displayed good contact action in the above test against *Aphis fabae*.

EXAMPLE 3

Action against *Chilo suppressalis*

Six rice plants at a time of the variety Caloro were transplanted into plastic pots (diameter at the top = 17 cm) and reared to a height of about 60 cm. Infestation with *Chilo suppressalis* larvae ($L_1$: 3-4 mm long) took place 2 days after the active substance had been applied in granule form to the paddy water (rate of application: 8 kg of active substance per hectare). Evaluation of the insecticidal action took place 10 days after application of the granules.

The compounds according to Example 1 displayed good action in the above test against *Chilo suppressalis*.

EXAMPLE 4

Action against ticks

A. *Rhipicephalus bursa*

Five adult ticks or 50 tick larvae were counted into a glass tube and immersed for 1 to 2 minutes in 2 ml of an aqueous emulsion from an emulsion series each containing 100, 10, 1 and 0.1 ppm of test substance. The tube was then sealed with a standardised cotton wool plug and placed on its head, so that the active substance emulsion could be absorbed by the cotton wool. In the case of the adults evaluation took place after 2 weeks, and in that of the larvae after 2 days. Each test was repeated twice.

B. *Boophilus microplus* (larvae)

Tests were carried out in each case with 20 OP-sensitive larvae using an analogous dilution series as in the case of test A. (The resistence refers to the tolerability of Diazinon). The compounds according to Example 1 displayed good action in the above test against adults and larvae of *Rhipicephalus bursa* and sensitive and OP-resistent larvae of *Boophilus microplus*.

EXAMPLE 5

Acaricidal action

*Phaseolus vulgaris* (dwarf beans) had an infested piece of leaf from a mass culture of *Tetranychus urticae* placed on them 12 hours before the test for the acaricidal action. The mobile stages which have migrated were sprayed with the emulsified test preparations from a chromatography atomiser so that the spray broth did not run off. The number of living and dead larvae, adults and eggs were evaluated after 2 to 7 days under a stereoscopic microscope and the result expressed in percentages. During the "interim", the treated plants were kept in greenhouse compartments at 25°C.

The compounds according to Example 1 displayed good action in the above test against eggs, larvae and adults of *Tetranychus urticae*.

We claim:

1. A compound of the formula

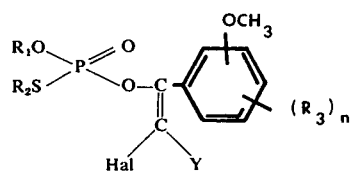

wherein $R_1$ is methyl or ethyl; $R_2$ is propyl or butyl; each $R_3$ is hydrogen, chlorine or bromine; $n$ is 1 or 2; $y$ is hydrogen or chlorine; and Hal is chlorine or bromine.

2. A compound according to claim 1 in which $R_2$ is n-propyl, sec.butyl or isobutyl.

3. The compound according to claim 2 which is O-ethyl-S-n-propyl-O-[1-(2-methoxy-5-chlorophenyl)-2,2-dichlorovinyl]-thiolphosphate.

4. The compound according to claim 2 which is O-ethyl-S-n-propyl-O-[1-(4-methoxy-3-chlorophenyl)-2,2-dichlorovinyl]-thiolphosphate.

5. The compound according to claim 2 which is O-ethyl-S-n-propyl-O-[1-(4-methoxy-2-chlorophenyl)-2,2-dichlorovinyl]-thiolphosphate.

6. The compound according to claim 2 which is O-ethyl-S-n-propyl-O-[1-(2-methoxy-5-bromophenyl)-2,2-dichlorovinyl]-thiolphosphate.

7. The compound according to claim 2 which is O-ethyl-S-n-propyl-O-[1-(2-methoxy-5-chlorophenyl)-2-chlorovinyl]-thiolphosphate.

8. The compound according to claim 2 which is O-ethyl-S-n-propyl-O-[1-(4-methoxy-2-chlorophenyl)-2-chlorovinyl]-thiolphosphate.

9. The compound according to claim 2 which is O-ethyl-S-n-propyl-O-[1-(2-methoxy-5-bromophenyl)-2-chlorovinyl]-thiolphosphate.

10. The compound according to claim 2 which is O-ethyl-S-n-propyl-O-[1-(4-methoxy-2,5-dichlorophenyl)-2-chlorovinyl]-thiolphosphate.

* * * * *